United States Patent
Birckbichler et al.

(10) Patent No.: US 7,374,713 B2
(45) Date of Patent: *May 20, 2008

(54) METHOD FOR MANUFACTURING AND INSPECTING BLOW-MOLDED PLASTIC CONTAINERS

(75) Inventors: Craig Alan Birckbichler, Chicora, PA (US); Sudha Christy Jebadurai, Poland, OH (US); Georg V. Wolfe, Butler, PA (US); Ronald A. Puvak, Butler, PA (US); William E. Schmidt, Gibsonia, PA (US)

(73) Assignee: AGR International, Inc., Butler, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/543,438

(22) Filed: Oct. 5, 2006

(65) Prior Publication Data

US 2007/0029707 A1 Feb. 8, 2007

Related U.S. Application Data

(63) Continuation of application No. 11/041,565, filed on Jan. 24, 2005, which is a continuation of application No. 10/106,263, filed on Mar. 26, 2002, now Pat. No. 6,863,860.

(51) Int. Cl.
*B29C 49/78* (2006.01)
(52) U.S. Cl. .............. 264/410; 264/40.1; 264/523; 425/141; 425/174.4; 425/538
(58) Field of Classification Search ........ 264/410, 264/40.1, 523; 425/141, 174.4, 538
See application file for complete search history.

(56) References Cited

U.S. PATENT DOCUMENTS 3,439,178 A 4/1969 Rottmann (Continued)

FOREIGN PATENT DOCUMENTS

DE 3611536 A1 10/1987

(Continued)

OTHER PUBLICATIONS

AGR-TOPWAVE, LLC, Pet Wall, pp. 1-2, Butler, PA, USA.

(Continued)

*Primary Examiner*—Suzanne E. McDowell
(74) *Attorney, Agent, or Firm*—Kirkpatrick & Lockhart Preston Gates Ellis LLP

(57) ABSTRACT

A method of manufacturing plastic containers. The method may comprise the steps of (1) forming a plastic container from a preform in a blow-molder, where the blow-molder comprises a plurality of molds and spindles; and (2) inspecting the plastic container after formation in the blow-molder. The containers are inspected by impinging infrared light thereon and detecting the portion of the infrared light that passes through the container and converting the same into corresponding electrical signals which are delivered to a microprocessor. The microprocessor receives signals from sensors associated with the blow-molder relating to the position of the molds, the identity of the molds and the identity of the spindles in order that the information that is determined by inspection can be associated with specific molds and spindles. The information may be visually displayed so as to provide feedback regarding the inspection process. In a preferred embodiment wall thickness measurements are taken at several vertically spaced positions simultaneously. Corresponding apparatus is provided.

53 Claims, 6 Drawing Sheets

U.S. PATENT DOCUMENTS

| | | | |
|---|---|---|---|
| 3,456,788 A | 7/1969 | Stapf et al. | |
| 3,729,632 A | 4/1973 | Cho et al. | |
| 3,827,812 A | 8/1974 | Heimann | |
| 3,923,158 A | 12/1975 | Fornaa | |
| 3,980,890 A | 9/1976 | Heckrodt et al. | |
| 4,304,995 A | 12/1981 | Huttunen et al. | |
| 4,332,606 A | 6/1982 | Gardner | |
| 4,393,305 A | 7/1983 | Shimizu et al. | |
| 4,476,533 A | 10/1984 | Daudt et al. | |
| 4,490,612 A | 12/1984 | Tormala | |
| 4,639,263 A | 1/1987 | Kulikauskas | |
| 4,691,830 A | 9/1987 | Ahl et al. | |
| 4,762,544 A | 8/1988 | Davey | |
| 5,139,406 A | 8/1992 | Hoshino et al. | |
| 5,437,702 A * | 8/1995 | Burns et al. | 65/29.12 |
| 5,591,462 A | 1/1997 | Darling et al. | |
| 6,863,860 B1 | 3/2005 | Birckbichler et al. | |
| 6,872,895 B2 | 3/2005 | Cockran et al. | |
| 6,985,221 B2 * | 1/2006 | Semersky et al. | 356/239.6 |
| 2003/0223086 A1 | 12/2003 | Semersky et al. | |

FOREIGN PATENT DOCUMENTS

| | | |
|---|---|---|
| EP | 0348524 A1 | 1/1990 |
| WO | WO 01/65204 A1 | 9/2001 |

OTHER PUBLICATIONS

AGR-TOPWAVE, LLC, Profiler Guage PG 9800, pp. 1-4, Butler, PA USA.

Zarnick, K., "100% On-Line Inspectino for the Pet Container-Industry", SPE Conference/Plastics West, Las Vegas, NV, Oct. 4, 1990 and SPE Conference, Belin, Germany, Oct. 22,25, 1990, pp. 1-7, Figs. 1-7 (18 pages total).

Puvak, R., "Improving Production Performance of PET Containers through the use of On-Line Inspection Systems", pp. 1-8, Figures 1-8 (19 pages total).

Tormala, S., "High Performance Plastic Packaging", Society fo Plastics Engineers International, Oct. 31-Nov. 1, 1989, pp. 1-8, 8 tests.

Adolfs, F., ESPRIT, KB-MUSICA (2671), plas. 140.KRP.1, Sep. 19, 1989, pp. 1-10, Figs. 1-5.

Puvak, R., Improving PET Production Efficiencies via on-Line Inspection and Rejection fo Defective Preforms and Finished Containers, pp. 1-10, Figs. 1-8.

* cited by examiner

METHOD FOR MANUFACTURING AND INSPECTING BLOW-MOLDED PLASTIC CONTAINERS

CROSS REFERENCE TO RELATED APPLICATIONS

The present application is a continuation of U.S. patent application Ser. No. 11/041,565, entitled "Method and apparatus for monitoring wall thickness of blow-molded plastic containers," filed Jan. 24, 2005, which is a continuation of U.S. patent application Ser. No. 10/106,263, entitled "Method and apparatus for monitoring wall thickness of blow-molded plastic containers," filed Mar. 26, 2002, now U.S. Pat. No. 6,863,860.

BACKGROUND OF THE INVENTION

It has long been known that plastic containers such as bottles must be inspected in order to make sure that the wall thickness is adequate for the desired purpose and that the use of excess material is minimized.

In general, it has been known to employ sampling inspection techniques wherein, at a periodic intervals, which might be on the order of once per hour, a container was removed from the conveyance system after the container emerged from the blow-molder and was destructively tested by cutting the same into multiple, horizontal sections which were then weighed with the weight being correlated with the wall thickness.

An alternative inspection method involved measuring the wall thickness of such containers by nondestructively testing sample plastic containers. A suitable system for effecting such testing is the AGR Top Wave Profiler Gauge PG 9800. A suitable laboratory instrument for this latter approach is that sold under the trademark AGR Top Wave Wall Thickness Profiler. One of the problems with such an inspection approach is that it was time-consuming and labor intensive. Also, the long interval between samplings resulted in a delay in process feedback which in turn could result in reduced production efficiencies.

It has also been known to employ high-speed on-line wall thickness monitoring systems for blow-molded plastic containers. These systems provide real-time monitoring of material distributions and rejection of defects. A suitable system for such purpose is that sold under the trademark AGR Top Wave PET Wall System. While these systems represent a substantial improvement in the completeness of sampling by inspecting each container and the timing of same, they did not provide feedback coordinated with the operation of the blow-molding machine.

U.S. Pat. No. 4,304,995 discloses a system for measuring wall thickness of plastic containers employing infrared absorption. The containers are sampled off-line and required the use of rotation and disclosed the use of radiation sources and radiation detectors which were structured to rotate with respect to each other.

U.S. Pat. No. 4,490,612 discloses a method of measuring the thickness of plastic film using relative absorptions of two infrared wavelengths.

U.S. Pat. No. 5,139,406 discloses the use of infrared absorption in measuring the wall thickness of plastic containers. On-line measurement is contemplated, but this system requires insertion of a probe into the container. Such an approach is uneconomical and inefficient in respect of current blow-molder plastic container production speeds.

U.S. Pat. No. 5,591,462 discloses the use of machine vision technology in monitoring certain defects in blow-molded containers. Among the features being monitored by this system are seal surface, base and neck folds and finish gauge inspection.

PCT publication WO 01/65204 discloses a method and apparatus for measuring plastic containers on-line employing infrared absorption. The apparatus was said to be employable on a conveyer or inside the blow-molder. It made use of laterally homogenous material distribution properties and measured though both sides of the container.

In spite of the foregoing prior art disclosures, there remains a very real and substantial need for an improved inspection system for blow molded plastic containers which will provide timely and accurate feedback regarding not only whether a container fell within the wall thickness specifications, but also identity of the molds and associated spindles which produced the container.

SUMMARY OF THE INVENTION

In one general aspect, the present invention directed to a method involving the inspection of the wall thickness of blow-molded plastic containers by providing a plastic container blow-molder having a plurality of molds and a plurality of associated spindles. The containers are inspected by impinging infrared light thereon and detecting the portion of the infrared light that passes though the container and converting the same to corresponding electrical signals which are delivered to a microprocessor. The microprocessor receives the thickness related signals and compares them with stored information regarding the desired thickness and emits thickness information. A visual display of such information, which may include an average container wall thickness over a period of time, for each mold and spindle may be provided.

The method may involve providing a plurality of such systems so that container wall thickness may be measured substantially simultaneously at a plurality of elevations.

The method includes sensing a plurality of conditions in the blow-molder, including mold position, mold identity and spindle identity such that the thickness determined can be synchronized with a particular mold and spindle to thereby provide meaningful feedback regarding the thickness determination.

The presence of a container to be inspected in the inspection station is also provided. A reject mechanism for physically removing a rejected container is also provided.

In another general aspect, the present invention is directed to an apparatus for inspecting blow-molded plastic containers. The apparatus may include an inspection station preferably disposed inside of the blow-molder and having at least one source of infrared radiation which impinges the radiation on the plastic container to be inspected and cooperating photodetectors which may be photoconductive lead-sulfide infrared detectors, for example. These receive the infrared radiation passing through the container and convert the same into corresponding electrical signals which are delivered to the microprocessor. The microprocessor contains stored information regarding the desired thickness and is structured to effect a comparison and issue thickness information output signals which may go to a visual display unit for presentation to an operator and may also, if the container is to be rejected, present such a signal to the reject mechanism which will remove the container from the line. Sensors for sensing the mold assembly position, as well as the identity of each mold and spindle so as to synchronize the same with the container being inspected are provided and are preferably disposed within the blow-molder.

In another general aspect, the present invention is directed to a method of manufacturing plastic containers. The method may comprise the steps of (1) forming a plastic container from a preform in a blow-molder, where the blow-molder comprises a plurality of molds and spindles; and (2) inspecting the plastic container after formation in the blow-molder. The step of inspecting the plastic container may comprise directing light energy from at least one light energy source from an exterior of the plastic container toward the plastic container after formation of the plastic container by the blow-molder and sensing, with at least one light energy sensor operatively associated with the at least one light energy source, a portion of the light energy that passes through the plastic container. The step of inspecting may also comprise generating a signal from the sensed portion of the light energy that passes through the plastic container that is related to the light energy absorbed by the plastic container and inputting the signal related to the light energy absorbed by the plastic container to a microprocessor. The step of inspecting may also comprise inputting, to the microprocessor, at least one timing signal indicative of the mold and spindle of the blow-molder involved in the formation of the plastic container. The step of inspecting may also comprise determining, by the microprocessor, a container attribute of the plastic container based on the signal related to the light energy absorbed by the plastic container and determining, by the microprocessor, the mold and spindle of the blow-molder involved in forming the plastic container based on the at least one timing signal.

According to various implementations, the container attribute may be the sidewall thickness of the plastic container. Also, the manufacturing method may also comprise adjusting a parameter of the blow-molder based on the inspection. Further, the method may also comprise rejecting the plastic container if it does not pass the inspection by separating the plastic container from non-rejected plastic containers. In addition, the method may comprise visually displaying information about the inspection on a display. The displayed information may include information associating the container attribute with identification of the mold and spindle involved in the formation of the plastic container.

It is an object of the present invention to provide an improved automated on-line rapid inspection system for inspecting wall thickness of plastic containers, such as bottles, for example.

It is another object of the invention to provide a method an apparatus for effecting such inspection while providing meaningful feedback regarding the specific mold and spindle which made a given container.

It is another object of the present invention to provide such a system which employs sensors within the blow-molder to provide information to a microprocessor regarding mold position and mold and spindle identity as related to a specific blow-molded container.

It is an object of the present invention to provide a system which is adapted for rapid on-line assembly of plastic bottles and other plastic containers made by blow-molding in such a manner as to identify the mold and spindle which made a specific container.

It is a further object of the present invention to provide such a system which will facilitate immediate communication of wall thickness information for either manual or automated control of the blow-molding system.

It is a further object of the invention to provide such a system which enhances the efficiency of the manufacture of blow-molded plastic containers.

These and other objects of the present invention will be more fully understood from the following description of the invention on reference to the illustrations appended hereto.

DESCRIPTION OF THE PREFERRED EMBODIMENTS

As employed herein, the term "containers" refers to plastic bottles, jars, vials and other plastic containers usable for storage of liquid and other flowable materials. Examples of the size of containers for which the present invention is particularly well suited are containers having a capacity of about 0.2 to 3 liters.

In a typical prior art plastic container, blow-molding process preforms entering the blow-molder are typically at room temperature. The preforms are inverted and loaded, upside-down, onto spindles. The spindles carry the preforms through the reheat oven which raises the temperature of the plastic in preparation for blow-molding. Uniform heating is important so the spindles rotate as they traverse through the oven. There are typically 100 to 400 spindles, forming a conveyor loop. After exiting the reheat oven, the preforms are removed from the spindles and transferred by a system of transfer wheels into the molds on the mold wheel. Failure of the spindles to rotate correctly while traversing through the oven will result in a poor thickness distribution in the blown container.

Employing one or more light sources of infrared radiation and cooperating associated photodetectors preferably located within the blow-molder near the output portion of a blow-molder where the containers are extracted from the molds, container wall thickness can readily and rapidly be determined. It is known that plastic materials such as PET absorb infrared radiation of specific wavelengths. This facilitates determination of the thickness of the container wall based on the amount of infrared radiation that has been absorbed. In a preferred practice of the present invention, the thickness monitoring apparatus and method will employ two distinct infrared wavelengths in order to compensate for refractive and scattering effects that might otherwise have a deleterious effect on the measurement.

Figure 1:
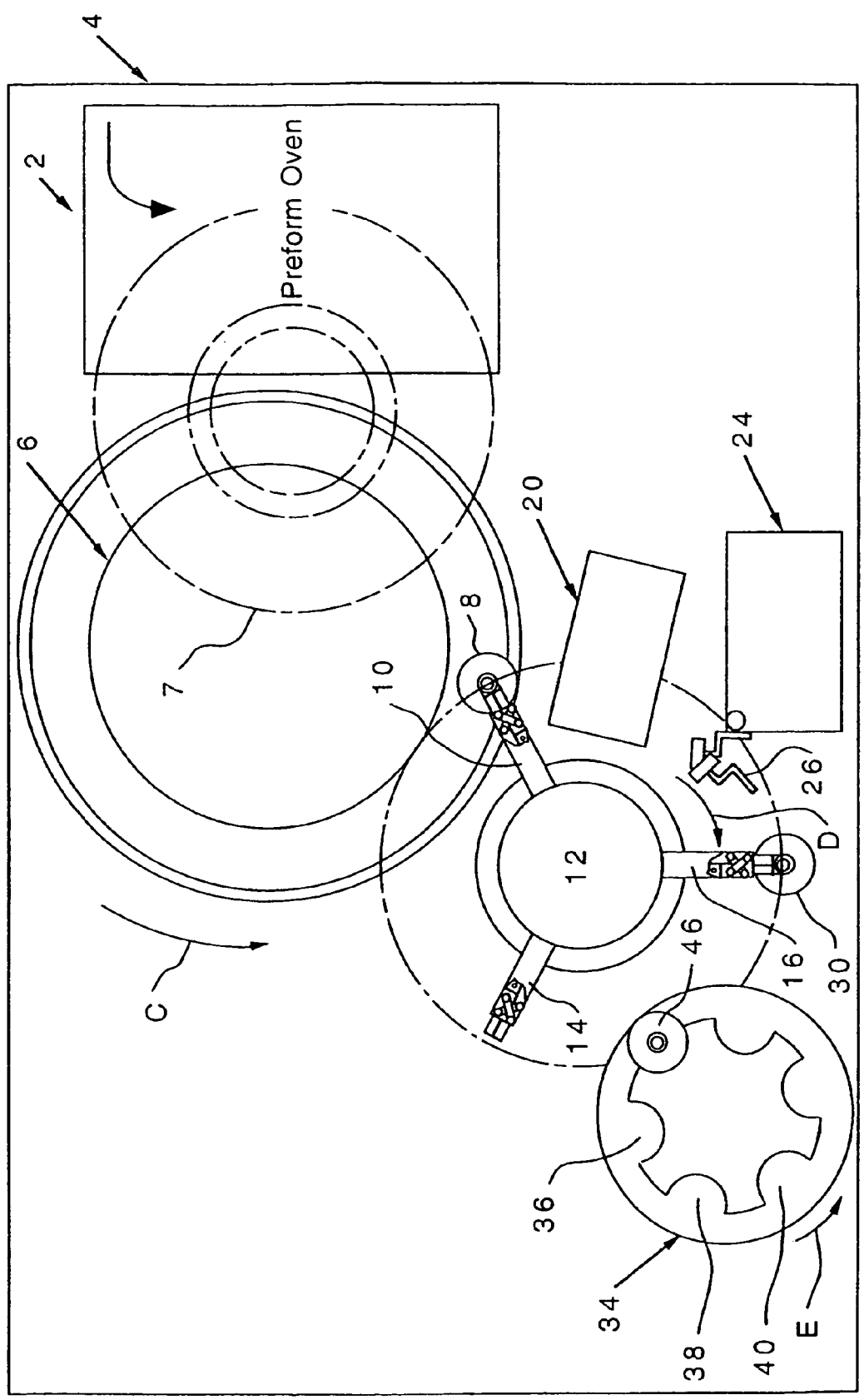
FIG. 1 is a schematic plan view showing the blow-molder, container transporting mechanisms, the inspection area and reject area.

Referring to FIG. 1, a preform oven 2 typically carries the plastic preforms on spindles through the oven section so as to preheat the preforms prior to blow-molding of the containers. The preforms leaving the preform oven 2 enter the mold assembly 6 which contains a plurality of molds by means of conventional transfer apparatus 7 (shown in phantom). The blow-molder 4, which may be of conventional type, has the array of molds which may be on the order of ten to twenty-four arranged in a circle and rotating in a direction indicated by the arrow C. Containers emerging from the mold assembly 6, such as container 8, will be suspended from a transfer arm, such as 10, on transfer assembly 12 which is rotating in the direction indicated by arrow D. Similarly, transfer arms 14 and 16 will, as the transfer assembly 12 rotates, pick up a container such as 8 and transport it through the inspection area 20 which will be described in greater detail hereinafter. A reject area 24 has a reject mechanism 26 which will physically remove from the transfer assembly 12 any containers deemed to be rejects. Container 30 has passed beyond the reject area 24 and will be picked up in star wheel 34 which is rotating in direction E and has a plurality of pockets, such as 36, 38, 40, for example. Container 46 is shown as being present in such a star wheel pocket. The containers will then be transferred in a manner known to those skilled in the art to conveyer means according to the desired transport path and nature of the system.

Figure 2:
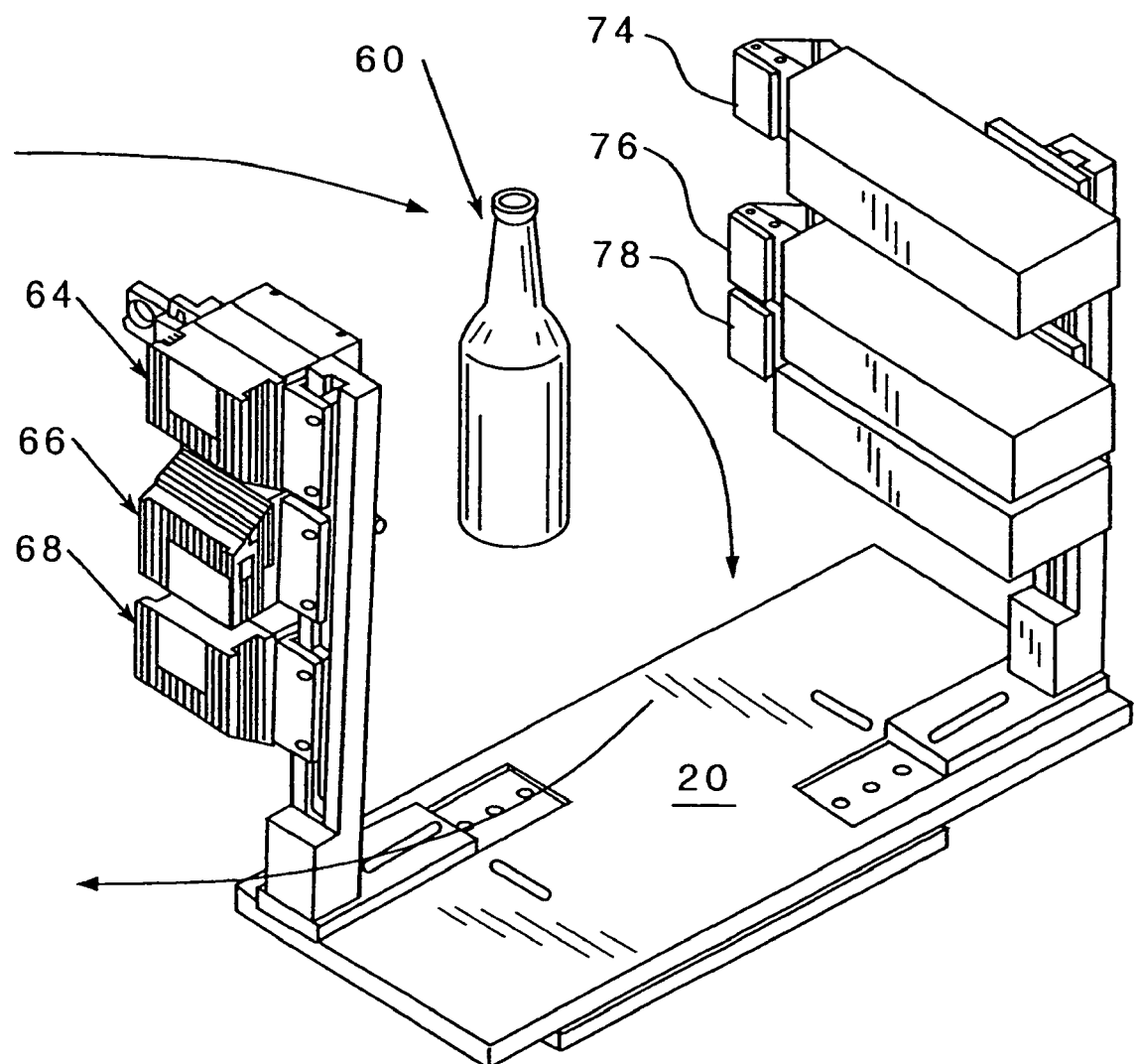
FIG. 2 is a perspective view showing a form of light source and associated photodetector employable in the inspection station of the present invention.

Referring to FIG. 2, there is shown a form of inspection station 20 which has a container 60 passing therethrough in the direction indicated by the arrow under the influence of a suitable conveyance device (not shown). In the form shown, a plurality of light sources 64, 66, 68 are vertically spaced from each other in order to inspect the wall thickness of the bottle at three zones at three different elevations. Cooperating with the light sources 64, 66, 68, respectively, are photodetectors 74, 76, 78. In operation, infrared radiation will be emitted by the light sources 64, 66 68, impinge upon bottle 60, have a portion of the infrared radiation absorbed by the plastic container 60 and have the remaining infrared radiation impinge upon the detectors 74, 76, 78 which will convert the received light into a corresponding electrical signal which will be delivered to a microprocessor for further processing. Any suitable detector which will function efficiently with the infrared radiation wavelengths employed may be used. A preferred detector is a photoconductive lead-sulfide (PbS) infrared detector. A suitable PbS detector is that sold by CalSensors. In a preferred system, the detector assembly consists of a prism-grating-prism spectrograph and two or more PbS detectors (such an assembly is manufactured by Spectral Imaging, Ltd. Of Finland, using PbS detectors from CalSensors). The spectrograph disperses the infrared radiation as a function of wavelength; the detectors are located so as to be sensitive to specific wavelengths of infrared radiation. One wavelength is selected to correspond to an absorption band in the plastic container. A second wavelength is selected to correspond to a transmission band in order to provide a reference. As an alternative to using the spectrograph, band-pass optical filters may be used in conjunction with the PbS detectors.

Referring still to FIG. 2, further details regarding the creation of synchronized wall thickness determination as related to specific molds and spindles will be considered. The light source preferably includes a halogen bulb that is always on, a lens to collect and collimate the light into a beam, a spinning segmented disk that "chops" the light beam and a remotely-controlled calibration disk. The light source is preferably always "on," emitting a pulsed beam (which preferably pulses at about 600 Hz). The light source emits a pulsed beam of "white" light, containing all of the desired infrared wavelengths.

Figure 3:
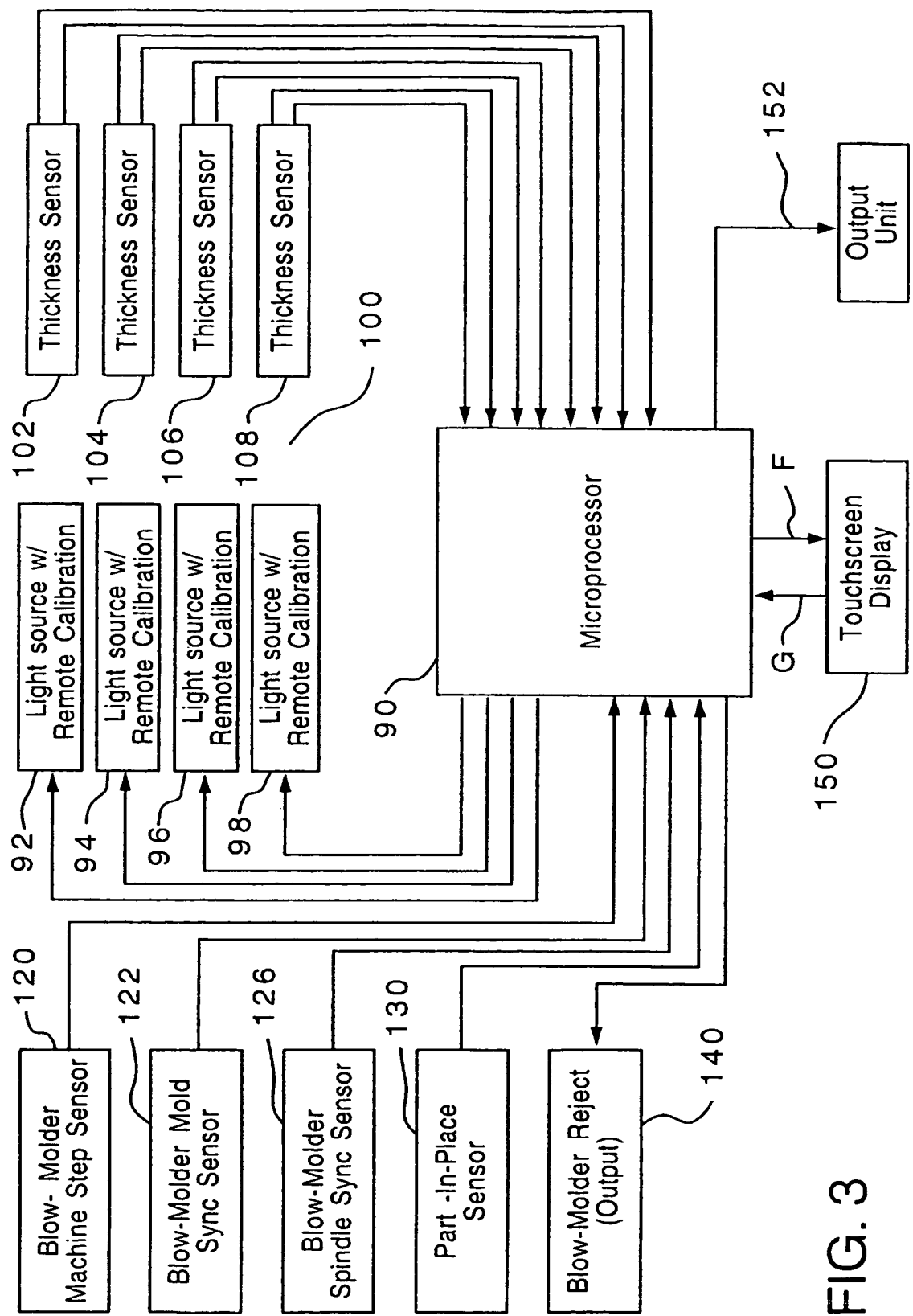
FIG. 3 is a schematic diagram showing a form of apparatus usable in the present invention and the interaction of the same.

Referring to FIG. 3, there is shown a microprocessor 90 which, in the form shown, exercises control over the calibration disks, which are preferably integral with light sources 92, 94, 96 and 98. A container which will pass through the gap indicated generally as 100 will, in the form shown, receive light from sources 92, 94, 96 98, absorb a portion of the same and then have the light not absorbed impinge on photodetector sensors 102, 104, 106 108, respectively, which will convert the received light into corresponding electrical signals which are delivered to the microprocessor 90.

In a preferred embodiment of the invention, three key sensors which are within or operatively associated with the blow molder, provide information to enable synchronization of the specific molds and spindles which made the container being inspected and thereby provide valuable feedback information. One sensor, designated the blow-molder machine step sensor 120, emits a signal which contains information regarding the counting of the molds and spindles from their corresponding starting position. The total number of molds or spindles may vary depending upon the make and model of blow-molder, but this information is known in advance. This information may be programmed into the system. A second signal, which is from the blow-molder synchronization sensor 122, provides information regarding start of a new cycle of rotating the mold assembly. The output of this sensor 122 is provided to microprocessor 90. The blow-molder spindle synchronizing sensor 126 provides output regarding the new cycle of rotating the spindle assembly. This output is provided to the microprocessor 90. The sensors employed for monitoring machine step mold sync and spindle sync may be positioned at any suitable location within the blow-molder and may be of any suitable type, such as inductive sensors which are well known to those skilled in the art.

The part-in-place sensor 130 provides a signal to the computer indicating that a container has arrived at the inspection station and that the wall thickness inspection should be initiated. At that point, the container transects the beams of white light containing all of the desired infrared wavelengths emitted by light sources 92, 94, 96, 98. The system preferably employs an incandescent light bulb that is operated in a continuous mode. This continuous light is preferably mechanically shuttered at the desired 600 Hz by a rotating segmented disk contained in the light source assembly. The output of the light source is a pulsed beam of light. This pulsed radiation is designed to match the characteristics of the detectors. The microprocessor 90 receives the electrical signal and affects a comparison of the thickness information contained within the electrical signal with stored information regarding desired thickness. If the thickness is not within the desired range, it emits a signal to the blow-molder reject 140 which in turn initiates a rejection signal to operate rejection apparatus 24, 26 (FIG. 1) and discard that container from the conveyer. The output thickness information from the microprocessor 90 will be delivered to touchscreen display 150 which provides an operator with information regarding specific containers produced by particular mold and spindle combinations. It is preferred that the values be averaged over a period of time which may be on the order of 30 seconds to ten minutes. In addition or in lieu of time measurement, the average may be obtained for a fixed number of containers which may be on the order of 2 to 2500. The operator also obtains trend information for the blow-molder and individual molds and spindles through the visual display unit 150. In the event of serious problems requiring immediate attention, visual and/or audio alarms may be provided. As indicated by the dual arrows F and G, an operator may input certain information to the microprocessor 90 to alter calibrations in order to control operation of the microprocessor. The operator may input process limits and reject limits into the microprocessor 90 for each of the thickness measurement zones. The reject limits are the upper and lower thickness values that would trigger the rejection of a container. The process limits are the upper and lower values for the time-averaged or number of container averaged thickness that would trigger a process alarm indicator. Also, if desired, hard copy or other output of the microprocessor 90 results may be provided as by output 152 which may be a conventional printer, for example.

The microprocessor 90 display highlights molds or spindles having undesirable thickness—either too thick or too thin. For example, if one mold was producing containers that are too thick or too thin, the operator would adjust mold-related parameters such as blow-pressure or blow-rate to correct the problem; or the operator might need to stop the blow-molder to replace or repair an air valve for that mold. It will be appreciated that the mold/spindle-correlated feedback provided by the microprocessor is used to localize the problem.

Figure 4:
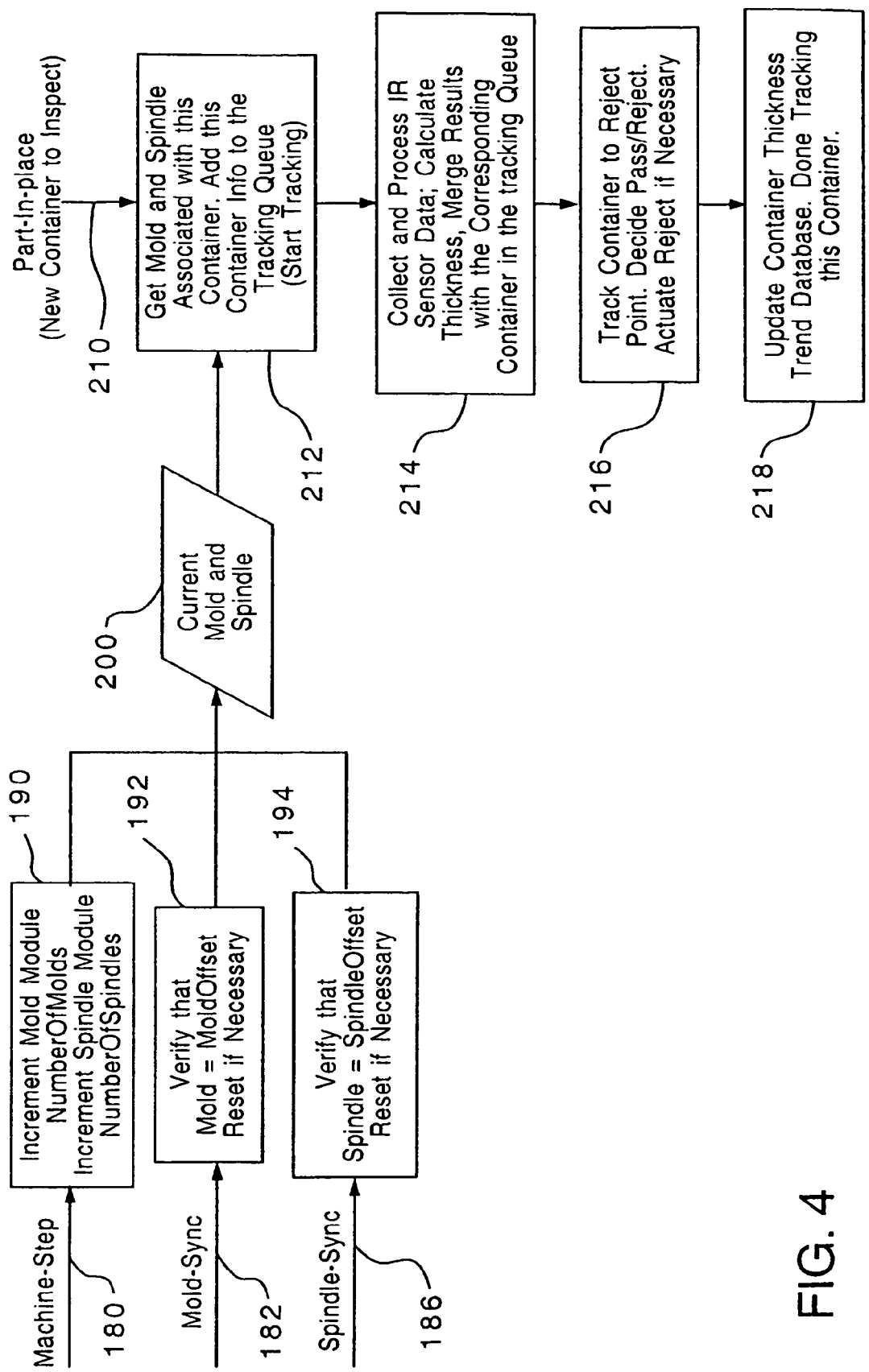
FIG. 4 is an algorithm flow chart illustrating the flow of information in an embodiment of the present invention.

Referring to FIG. 4, an algorithm flow chart showing the method of the inspection process, container tracking and combining mold and spindle information of the present invention will be considered. As indicated in FIG. 3, the blow-molder machine step sensor 120 will provide an output identified in FIG. 4 as 180 and the blow-molder mold sync sensor 122 will provide an output signal 182 and the blow-molder spindle sync sensor 126 will provide a spindle sync signal 186. As shown by block 190, the machine step signal 180 contains information regarding the incremental movement of the mold module, the number of molds and the incremental spindle module and the number of spindles. The mold sync signal 182 will verify that the mold is equal to the mold offset with resetting being accomplished if necessary.

In order to adjust for the fact that microprocessor 90 may start up in the middle of a blow-molding cycle, the microprocessor 90 preferably employs an algorithm that allows the microprocessor to re-synchronize with the blow-molder 4 within one mold or spindle cycle. The microprocessor 90 then remains synchronized with the blow-molder 4. The algorithm is:

Machine-step event: increment mold#, if mold# is greater than number of molds, reset to 1 increment spindle#, if spindle# is greater than number-of-spindles, reset to 1

Mold-sync event: Set mold# to X (mold offset as pre-configured)

Spindle-sync event: Set spindle# to Y (spindle offset as pre-configured)

Similarly, the spindle sync signal 186 will verify that the spindle equals the spindle offset with a reset being achieved, if necessary. The collective output of blocks 190, 192 and 194 is detailed information with respect to the current mold and spindle identity and position with respect to the container being inspected. The sensor 130 (FIG. 3), when a container has reached the inspection level will emit signal 210 which is combined in block 212 by associating the specific mold and signal with this particular container and this container is tracked in synchrony with the specific mold and spindle. In the next process block 214, the microprocessor will collect and process the infrared sensor data, calculate the thickness and merge the results with the corresponding container in the tracking queue.

The output of block 214 proceeds to block 216 where, if the container is being rejected, it is tracked to the rejection point and a decision regarding pass and reject has been made.

Finally, the microprocessor in block 218 updates the container thickness trend database and communicates the thickness information to touchscreen display 150 (FIG. 3). This ends the tracking of that container. It will be appreciated that the net result is that the particular container being inspected is associated with a particular mold and associated spindle with a reject or pass decision determining whether the particular container remains in the conveying process or is excluded by the reject mechanism. The information also serves to update the thickness trend database as displayed in unit 150 and printed or otherwise stored or processed in output unit 152 (FIG. 3).

Figure 5:
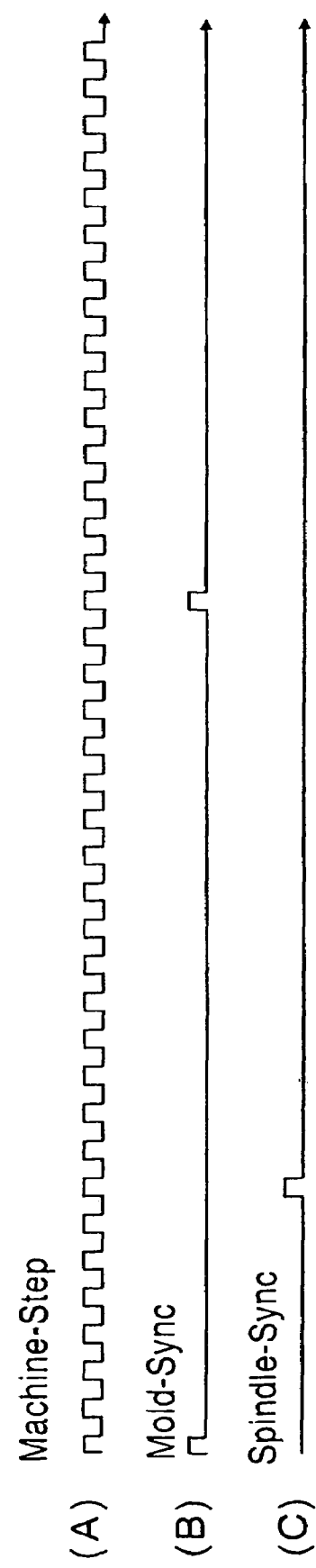
FIGS. 5(a), (b) and (c) illustrate a timing diagram showing the relationship among machine step, mold sync and spindle sync signals.

Referring to FIG. 5, there is shown in FIG. 5(A) the machine step timing diagram with there being a one-for-one correspondence between the machine step pulses and containers produced by the blow-molder. The mold sync pulse shown in FIG. 5(B) indicates the start of a new cycle of the mold wheel assembly and the spindle-sync pulse as shown in FIG. 5(C) shows the start of a new cycle of the spindle loop.

At the inspection station, there is a fixed phase relationship between the mold sync pulse and the machine step pulse corresponding to the first mold. This phase information, which may be referred to as the "MoldOffset," is determined when the system is installed into the blow-molder and then is entered into the processor. Similarly, the SpindleOffset is determined during installation and entered into the process.

Figure 6:
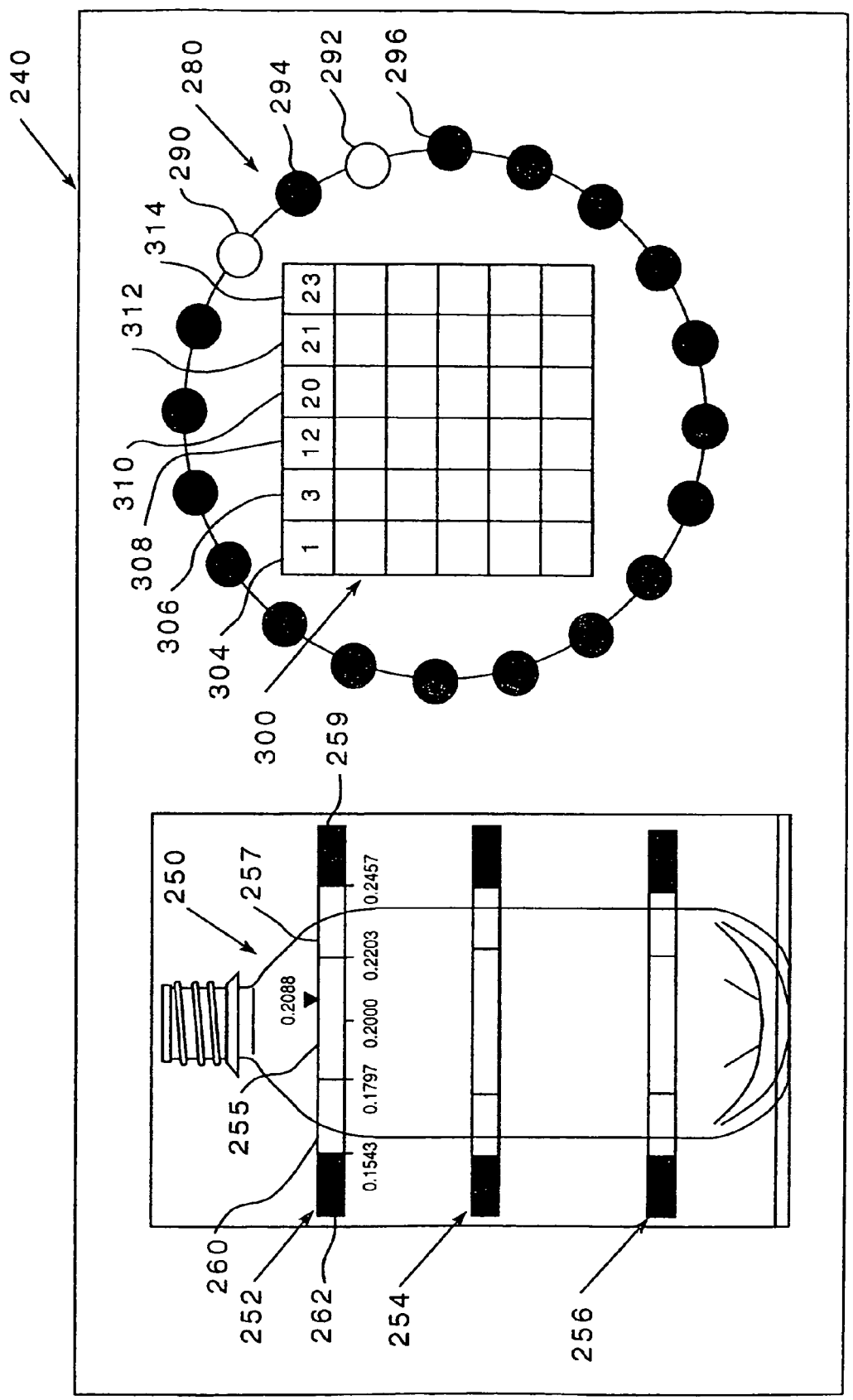
FIG. 6 illustrates a screen of a visual display unit employable in the present invention.

Referring to FIG. 6, there is shown a visual display screen 240 which could be presented on the touchscreen display unit 150 (FIG. 3) to provide prompt and concise feedback regarding the mold/spindle correlated thickness information for purposes of process control and blow-molder optimization. The process status is shown in FIG. 6. The representation on the left shows a container 250 which in the form shown is a bottle having an exteriorly threaded neck. The wall thickness has been measured at vertically spaced levels 252, 254, 256. Each band 252, 254, 256 will contain a numerical indication of the average wall thickness. These indicated numbers show the process-wide average thickness at these measurement locations averaged over a certain selected period of time which may be on the order of 30 seconds to 10 minutes or could be an average of a number of containers from about 2 to 2500.

Referring still to FIG. 6, it is noted by way of example that band 252 is subdivided into a plurality of units 255, 257, 259, 260, 262, each of which may be presented in a distinctive color different from next adjacent subportions of band 252 for ease of visual review. By way of example, the numbers underlying band 252 present a scale of thickness in inches taken to four decimal points. Overlying the band 252 appears the number 0.2088 with an inverted triangle pointing to a portion of band 252. This number represents an average wall thickness at that location of the bottle based on, for example, a period of time or a number of containers measured. One seeing the computer screen 240, therefore, can quickly ascertain not only quantitatively what the average thickness measurement has been, but also visually in terms of the position on the scale. Similar numerical scales and reading information would preferably be contained on bands 254, 256.

On the right in FIG. 6 is a graphic representation of the mold wheel assembly 280 having each mold represented by a circle and containing information regarding the related container thickness. In the center of the mold circle, there is a grid 300 showing container thickness status for a number of spindles. As the number of spindles can be quite large, the display shows a pareto-optimized list of problem spindles with the identity of the worst spindle problems being identified by a spindle number or other identifier.

With respect to the molds, it is noted that some indication regarding thickness may be provided by the use of different colors. For example, as shown, the number 290 points to a mold which has a white representation, as does 292. The remaining molds are shown in black. A suitable scale may be provided so that the white indicates a thickness above or below control limits and the black indicates a thickness within limits. As these circles may contain numbers (not shown) identifying a particular mold, this will enable an operator to obtain a visual indication regarding the average thickness as related to control limits or reject limits for that mold. With regard to spindle representing grid 300, as there are more spindles than shown in the grid, this embodiment would employ the worst of the spindles in respect of containers which have been inspected and having the greatest departure from desired wall thickness. By way of example, the top row of squares identified respectively by reference numbers 304, 306, 308, 310, 312, 314 are identified respectively and related to spindles 1, 3, 12, 20, 21, 23. As is true with the molds, these grid representations would preferably have color coding indicating as to each spindle in the grouping, the degree of departure from the control limits or reject limits or, in the event that it is within limits, a color indicating that category. It will be appreciated that while the drawings show color representations for the molds as being black or white, and no color distinctions are provided in the illustrated grid 300, two or more colors may be employed in respective circles and blocks to indicate various thickness averages as related to the desired limits.

If desired, additional information may be provided on the screen 240. For example, if the average is based upon a time of 3 minutes, a legend to that effect may be provided. Similarly, if the average thickness is based upon the last 250 bottles, a legend to this effect may be provided. Also, information regarding the total number of rejects and the percentage of rejects may be provided. Numerical indications of the number of rejects coming from each of the molds and spindles may also be provided. The color codes or symbols such as "+" or "−" may be employed to identify whether the departure from desired control limits or reject limits are above or below such limits.

Where two distinct wavelengths of infrared radiation are used, a first will be at a wavelength which is readily absorbed by the plastic material of the container and the other wavelength will be only slightly absorbed. A further possibility is that the containers may be filled with condensed water vapor at the end of the blow-molding process. If that is sufficiently dense, the internal fog formed in the container may scatter light away from the sensors and interfere with measurement. If desired, a third infrared wavelength which is not at an absorption band with respect to the plastic material can be used in order to calculate a correction factor to enhance the accuracy of the thickness measurement by correcting for optical scattering caused by the fog.

It will be appreciated that the present invention has provided an improved automated system for wall thickness determination in a plastic container which, as a result of sensors operatively associated with the blow-molder, provides detailed information so as to correlate wall thickness of a given container with the mold and spindle at which it is made. The microprocessor processes data regarding the thickness measurement and outputs the same to a unit which may visually display and/or to another unit which may provide hard copy of the average thickness readings which may also be a thickness reading achieved over a period of time such as about 30 seconds to 10 minutes or a number of containers which may be about 2 to 2500.

What is claimed is:

1. A method of manufacturing a plastic container comprising:
    forming the plastic container from a preform in a blow-molder, the blow-molder comprising a plurality of molds and spindles; and
    inspecting the plastic container after formation in the blow-molder, wherein inspecting the plastic container comprises:
        directing light energy from at least one light energy source from an exterior of the plastic container toward the plastic container after formation of the plastic container by the blow-molder;
        sensing with at least one light energy sensor operatively associated with the at least one light energy source a portion of the light energy that passes through the plastic container, wherein the at least one light energy source and the at least one light energy sensor are located in the blow-molder;
        generating a signal from the sensed portion of the light energy that passes through the plastic container that is related to the light energy absorbed by the plastic container;
        inputting the signal related to the light energy absorbed by the plastic container to a microprocessor;
        inputting, to the microprocessor, at least one timing signal indicative of the mold and spindle of the blow-molder involved in the formation of the plastic container;
        determining, by the microprocessor, a container attribute of the plastic container based on the signal related to the light energy absorbed by the plastic container; and
        determining, by the microprocessor, the mold and spindle of the blow-molder involved in forming the plastic container based on the at least one timing signal.

2. The method of claim 1, wherein the container attribute is average sidewall thickness.

3. The method of claim 1, further comprising adjusting a parameter of the blow-molder based on the inspection.

4. The method of claim 1 further comprising automatically rejecting the plastic container if it does not pass the inspection by separating the plastic container from non-rejected plastic containers.

5. The method of claim 1, further comprising visually displaying information about the inspection on a display.

6. The method of claim 5, wherein the displayed information comprises information associating the container attribute with identification of the mold and spindle involved in the formation of the plastic container.

7. The method of claim 1, wherein the step of determining the container attribute of the plastic container based on the signal related to the light energy absorbed by the plastic container comprises determining whether the container attribute is within desired limits based on the amount of light energy absorbed by the container.

8. The method of claim 1, wherein the step of directing light energy from the at least one energy source from the exterior of the plastic container toward the plastic container comprises directing light energy from the at least one energy source from the exterior of the plastic container toward the plastic container while the plastic container is suspended in an inspection area.

9. The method of claim 8, wherein the step of directing light energy from the at least one energy source from the exterior of the plastic container toward the plastic container comprises directing light energy from the at least one energy source from the exterior of the plastic container toward the plastic container while the plastic container is suspended in the inspection area by a transfer arm.

10. The method of claim 9, wherein the transfer arm comprises a rotating transfer arm.

11. The method of claim 10, further comprising adjusting a parameter of the blow-molder based on the inspection.

12. The method of claim 8, further comprising adjusting a parameter of the blow-molder based on the inspection.

13. A method of inspecting a plastic container formed by a blow-molder, wherein the blow-molder includes a plurality of molds for forming the plastic container, the method comprising:
   directing light energy from at least one light energy source from an exterior of the plastic container toward the plastic container after formation of the plastic container by the blow-molder;
   sensing with at least one light energy sensor operatively associated with the at least one light energy source a portion of the light energy that passes through the plastic container, wherein the at least one light energy source and the at least one light energy sensor are located in the blow-molder;
   generating a signal from the sensed portion of the light energy that passes through the plastic container that is related to the light energy absorbed by the plastic container;
   inputting the signal related to the light energy absorbed by the plastic container to a microprocessor;
   inputting, to the microprocessor, at least one timing signal indicative of the mold of the blow-molder involved in the formation of the plastic container;
   determining, by the microprocessor, a container attribute of the plastic container based on the signal related to the light energy absorbed by the plastic container; and
   determining, by the microprocessor, the mold of the blow-molder involved in formation of the plastic container based on the at least one timing signal.

14. The method of claim 13, further comprising adjusting a parameter of the blow-molder based on the inspection.

15. The method of claim 13 further comprising automatically rejecting the plastic container if it does not pass the inspection by separating the plastic container from non-rejected plastic containers.

16. The method of claim 13, further comprising visually displaying information about the inspection on a display.

17. The method of claim 16, wherein the displayed information comprises information associating the container attribute with identification of the mold involved in the formation of the plastic container.

18. The method of claim 13, wherein the step of determining the container attribute of the plastic container based on the signal related to the light energy absorbed by the plastic container comprises determining whether the container attribute is within desired limits based on the amount of light energy absorbed by the container.

19. The method of claim 13, wherein the step of directing light energy from the at least one energy source from the exterior of the plastic container toward the plastic container comprises directing light energy from the at least one energy source from the exterior of the plastic container toward the plastic container while the plastic container is suspended in an inspection area.

20. The method of claim 19, wherein the step of directing light energy from the at least one energy source from the exterior of the plastic container toward the plastic container comprises directing light energy from the at least one energy source from the exterior of the plastic container toward the plastic container while the plastic container is suspended in the inspection area by a transfer arm.

21. The method of claim 20, wherein the transfer arm comprises a rotating transfer arm.

22. The method of claim 21, further comprising adjusting a parameter of the blow-molder based on the inspection.

23. The method of claim 19, further comprising adjusting a parameter of the blow-molder based on the inspection.

24. An apparatus for inspecting a plastic container formed by a blow-molder, wherein the blow-molder includes a plurality of molds for forming the plastic container, the apparatus comprising:
   at least one light energy source for directing light energy from an exterior of the plastic container toward the plastic container after formation of the plastic container by the blow-molder;
   at least one light energy sensor operatively associated with the at least one light energy source for sensing a portion of the light energy that passes through of the plastic container and generating a signal from the sensed portion of the light energy that passes through the plastic container that is related to the light energy absorbed by the plastic container; and
   a microprocessor in communication with the at least one light energy sensor for:
      determining a container attribute of the plastic container based on the signal related to the light energy absorbed by the plastic container; and
      determining the mold involved in formation of the plastic container based on at least one timing signal received by the microprocessor, wherein the at least one timing signal is indicative of the mold involved in the formation of the plastic container, and wherein:
         the at least one light energy source is for directing light energy having two distinct infrared wavelengths toward the plastic container; and
         the at least one light energy sensor is for sensing, for each of the two distinct infrared wavelengths, the portion of the light energy that passes through the sidewalls of the plastic container.

25. The apparatus of claim 24, further comprising a reject mechanism in communication with the microprocessor for rejecting the plastic container when the microprocessor determines that the container attribute is not within a specified range.

26. The apparatus of claim 24, wherein the container attribute includes the thickness of the sidewalls of the plastic container.

27. The apparatus of claim 24, further comprising a display in communication with the microprocessor for displaying information correlating the container attribute to the mold involved in forming the plastic container.

28. The apparatus of claim 24, wherein:
   the at least one light energy source includes at least two vertically aligned light energy sources; and the at least one light energy sensor includes three at least two vertically aligned light energy sensors cooperatively associated with a corresponding one of the light energy sources.

29. The apparatus of claim 28, wherein the at least two light energy sensors comprise non-imaging sensors.

30. The apparatus of claim 24, wherein the at least one light energy source is positioned on a first side of a transport path for the plastic container and the at least one light energy sensor is on the opposite side of the transport path such that the plastic container passes between the at least one light energy source and the at least one light energy sensor.

31. The apparatus of claim 24, wherein the at least one timing signal includes a signal transmitted to the microprocessor by at least one of:
a blow-molder machine step sensor; and
a blow-molder mold synchronization sensor.

32. The apparatus of claim 24, wherein the at least one energy source is for directing light energy from the exterior of the plastic container toward the plastic container while the plastic container is suspended in an inspection area.

33. The apparatus of claim 32, wherein the at least one energy source is for directing light energy from the exterior of the plastic container toward the plastic container while the plastic container is suspended in the inspection area by a transfer arm.

34. The apparatus of claim 33, wherein the transfer arm comprises a rotating transfer arm.

35. The apparatus of claim 32, wherein the microprocessor is further for determining whether the container attribute is within desired limits based on the amount of light energy absorbed by the container.

36. An apparatus for inspecting a plastic container formed by a blow-molder, wherein the blow-molder includes a plurality of molds for forming the plastic container, the apparatus comprising:
at least three vertically aligned light energy sources for directing light energy from an exterior of the plastic container toward the plastic container after formation of the plastic container by the blow-molder;
at least three vertically aligned light energy sensors cooperatively associated with a corresponding one of the light energy sources for sensing a portion of the light energy that passes through of the plastic container and generating a signal from the sensed portion of the light energy that passes through the plastic container that is related to the light energy absorbed by the plastic container; and
a microprocessor in communication with the at least one three light energy sensors for:
determining a container attribute of the plastic container based on the signal related to the light energy absorbed by the plastic container; and
determining the mold involved in formation of the plastic container based on at least one timing signal received by the microprocessor, wherein the at least one timing signal is indicative of the mold involved in the formation of the plastic container.

37. An apparatus comprising:
a blow-molder comprising a plurality of molds and spindles for forming a plastic container from a preform;
an inspection device, located in the blow-molder, for inspecting the plastic container after formation by the blow-molder, wherein the inspection device comprises:
at least one light energy source for directing light energy from an exterior of the plastic container toward the plastic container after formation of the plastic container by the blow-molder;
at least one light energy sensor operatively associated with the at least one light energy source for sensing a portion of the light energy that passes through of the plastic container and generating a signal from the sensed portion of the light energy that passes through the plastic container that is related to the light energy absorbed by the plastic container; and
a microprocessor in communication with the inspection device for:
determining a container attribute of the plastic container based on the signal related to the light energy absorbed by the plastic container; and
determining the mold involved in formation of the plastic container based on at least one sensor signal received by the microprocessor.

38. The apparatus of claim 37, wherein:
the at least one light energy source comprises at least two vertically aligned light energy sources; and
the at least one light energy sensor comprises at least two vertically aligned light energy sources cooperatively associated with a corresponding one of the light energy sources.

39. The apparatus of claim 38, wherein the light energy sources comprises infrared light energy sources.

40. The apparatus of claim 39, wherein the light energy sensors comprise non-imaging sensors.

41. The apparatus of claim 39, wherein:
the at least two vertically aligned, infrared light energy sources are positioned on a first side of a transport path for the plastic container; and
the at least two vertically aligned light energy sensors are on an opposite side of the transport path such that the plastic container passes between the at least two light energy sources and the at least two light energy sensors.

42. The apparatus of claim 41, further comprising a transfer arm in the blow molder for transporting the plastic container along the transport path through the inspection device.

43. The apparatus of claim 42, wherein:
each of the at least two vertically, aligned infrared light energy sources are for directing light energy having two distinct infrared wavelengths toward the plastic container; and
each of the at least two vertically aligned light energy sensors are for sensing, for each of the two distinct infrared wavelengths, the portion of the light energy that passes through the sidewalls of the plastic container.

44. The apparatus of claim 42, wherein the microprocessor is further for determining whether the container attribute is within desired limits based on the amount of light energy absorbed by the container.

45. The apparatus of claim 44, further comprising a display in communication with the microprocessor for displaying information correlating the container attribute to the mold involved in forming the plastic container.

46. The apparatus of claim 45, wherein the microprocessor is further for determining the spindle involved in formation of the plastic container based on the at least one sensor signal received by the microprocessor.

47. The apparatus of claim 46, wherein the at least one sensor signal includes a signal transmitted to the microprocessor from the blow molder.

48. The apparatus of claim 47, wherein the at least one sensor signal includes at least one of:

a blow-molder machine step sensor; and a blow-molder mold synchronization sensor.

49. An apparatus comprising:

a blow-molder comprising a plurality of molds and spindles for forming a plastic container from a preform;

a transfer arm assembly in the blow-molder for transporting the plastic container along a transport path after formation by the blow-molder an inspection device, located in the blow-molder, for inspecting the plastic container along the transport path after formation by the blow-molder, wherein the inspection device comprises:

at least two vertically aligned light energy sources on a first side of the transport path for directing light energy from an exterior of the plastic container toward the plastic container after formation of the plastic container by the blow-molder;

at least two vertically aligned light energy sensors on a second side of the transport path opposite the first side, each of the at least two light energy sensors operatively associated with one of the at least two light energy sources, wherein the at least two light energy sensors are for sensing a portion of the light energy that passes through two sidewalls of the plastic container and generating signals from the sensed portion of the light energy that passes through the two sidewalls of the plastic container that is related to the light energy absorbed by the two sidewalls of the plastic container; and a microprocessor in communication with the inspection device for:

determining whether a container attribute of the plastic container based on the signals related to the light energy absorbed by the plastic container is within desired limits; and determining the mold involved in formation of the plastic container based on at least one sensor signal received by the microprocessor.

50. The apparatus of claim 49, wherein the microprocessor is further for determining the spindle involved in formation of the plastic container based on the at least one sensor signal received by the microprocessor.

51. A method of manufacturing a plastic container comprising:

forming the plastic container from a preform in a blow-molder, the blow-molder comprising a plurality of molds and spindles;

transporting the plastic container with a transfer along a transport path through an inspection station after formation of the plastic container by the blow-molder; and inspecting the plastic container as it passes through the inspection station, wherein inspecting the plastic container comprises:

directing light energy from an exterior of the plastic container toward the plastic container from at least two vertically arranged light energy sources on a first side of the transport path;

sensing with at least two vertically arranged light energy sensors a portion of the light energy that passes through two sidewalls of the plastic container, wherein each of the light energy sensors are operatively associated with one of the at least two light energy sources, wherein the at least two light energy sources and the at least two light energy sensors are located in the blow-molder;

generating signals from the sensed portion of the light energy that passes through the two sidewalls of the plastic container that is related to the light energy absorbed by the two sidewalls of the plastic container;

inputting signals related to the light energy absorbed by the plastic container to a microprocessor;

inputting, to the microprocessor, at least one sensor signal indicative of the mold involved in the formation of the plastic container;

determining, by the microprocessor, whether a container attribute of the plastic container based on the signals related to the light energy absorbed by the plastic container is within desired limits; and determining, by the microprocessor, the mold of the blow-molder involved in forming the plastic container based on the at least one sensor signal.

52. The method of claim 51, further comprising adjusting a parameter of the blow-molder based on the inspection.

53. The method of claim 52, further comprising, determining, by the microprocessor the spindle of the blow-molder involved in forming the plastic container based on the at least one sensor signal.

* * * * *